US010182851B2

(12) United States Patent
Robie et al.

(10) Patent No.: US 10,182,851 B2
(45) Date of Patent: Jan. 22, 2019

(54) ANGULATING BONE PLATE

(71) Applicant: FBC Device ApS, Risskov (DK)

(72) Inventors: Bruce H. Robie, North Andover, MA (US); Finn Bjarke Christensen, Silkeborg (DK); Jean Charles Le Huec, Pessac (FR)

(73) Assignee: FBC Device ApS, Risskov (DK)

( * ) Notice: Subject to any disclaimer, the term of this patent is extended or adjusted under 35 U.S.C. 154(b) by 393 days.

(21) Appl. No.: 14/950,074

(22) Filed: Nov. 24, 2015

(65) Prior Publication Data

US 2016/0143746 A1   May 26, 2016

Related U.S. Application Data

(60) Provisional application No. 62/083,763, filed on Nov. 24, 2014.

(51) Int. Cl.
*A61F 2/44* (2006.01)
*A61B 17/70* (2006.01)
*A61F 2/30* (2006.01)

(52) U.S. Cl.
CPC .......... *A61B 17/7059* (2013.01); *A61F 2/442* (2013.01); *A61F 2/4455* (2013.01);
(Continued)

(58) Field of Classification Search
None
See application file for complete search history.

(56) References Cited

U.S. PATENT DOCUMENTS 6,159,244 A * 12/2000 Suddaby ............... A61F 2/4455
606/247
6,332,895 B1 * 12/2001 Suddaby ............... A61F 2/4455
623/17.11
(Continued)

FOREIGN PATENT DOCUMENTS

| CN | 1816309 | 8/2006 |
| CN | 101715331 | 5/2010 |
| WO | WO 2016/085937 A2 | 6/2016 |

OTHER PUBLICATIONS

PCT International Search Report and Written Opinion for PCT/US2015/062341 dated Feb. 23, 2016.
(Continued)

*Primary Examiner* — Zade Coley
(74) *Attorney, Agent, or Firm* — McCarter & English, LLP

(57) ABSTRACT

An angulating spinal plate assembly for fixation and/or support of bones of the spinal column is provided. The angulating bone plate includes interleaved, arcuate sheets that facilitate relative motion between first/second elements. An implant assembly is also provided that includes an angulating bone plate and associated first/second intervertebral plates that extend therefrom. The angulating bone plate generally includes an interleaved elements, e.g., an upstanding tab that cooperates with opposing faces of an opening, that permit rotational movement as between first/second implant elements until a desired relative orientation is achieved. At such time, a fixation/locking element is generally employed to fix the first/second implant elements relative to each other. The rotational movement permitted is generally in multiple planes based on the cooperative arcuate surfaces provided in the disclosed elements, i.e., side-to-side and top-to-bottom freedoms of movement.

10 Claims, 11 Drawing Sheets

(52) U.S. Cl.
CPC ............ *A61F 2002/3093* (2013.01); *A61F 2002/30331* (2013.01); *A61F 2002/30578* (2013.01); *A61F 2002/30604* (2013.01); *A61F 2002/30784* (2013.01); *A61F 2002/4475* (2013.01)

(56) References Cited

U.S. PATENT DOCUMENTS

| | | | |
|---|---|---|---|
| 6,770,095 B2* | 8/2004 | Grinberg | A61F 2/4425 623/17.14 |
| 7,083,651 B2 | 8/2006 | Diaz et al. | |
| 7,270,679 B2* | 9/2007 | Istephanous | A61B 17/7049 623/17.11 |
| 7,666,185 B2 | 2/2010 | Ryan et al. | |
| 7,771,473 B2* | 8/2010 | Thramann | A61F 2/447 623/17.11 |
| 7,824,445 B2* | 11/2010 | Biro | A61F 2/44 623/17.15 |
| 7,842,037 B2 | 11/2010 | Schulze | |
| 7,931,688 B2* | 4/2011 | Landry | A61F 2/4465 623/17.11 |
| 8,007,536 B2 | 8/2011 | Christensen | |
| 8,057,547 B2* | 11/2011 | Hurlbert | A61F 2/4425 623/17.14 |
| 8,114,080 B2 | 2/2012 | Schulze | |
| 8,128,628 B2 | 3/2012 | Freid et al. | |
| 8,206,420 B2 | 6/2012 | Stern et al. | |
| 8,262,659 B2 | 9/2012 | Ryan et al. | |
| 8,636,773 B2 | 1/2014 | Stern et al. | |
| 8,784,419 B2 | 7/2014 | Overes et al. | |
| 8,894,711 B2* | 11/2014 | Varela | A61F 2/447 623/17.16 |
| 8,906,095 B2 | 12/2014 | Christensen et al. | |
| 2003/0074064 A1* | 4/2003 | Gerbec | A61F 2/4455 623/16.11 |
| 2003/0229348 A1 | 12/2003 | Sevrain | |
| 2003/0233146 A1 | 12/2003 | Grinberg et al. | |
| 2004/0006343 A1 | 1/2004 | Sevrain | |
| 2004/0019353 A1 | 1/2004 | Freid et al. | |
| 2004/0087947 A1* | 5/2004 | Lim | A61F 2/4465 606/247 |
| 2004/0092939 A1 | 5/2004 | Freid et al. | |
| 2004/0243241 A1 | 12/2004 | Istephanous et al. | |
| 2005/0004595 A1 | 3/2005 | Boyle et al. | |
| 2005/0107880 A1 | 5/2005 | Shimp et al. | |
| 2005/0197703 A1 | 9/2005 | Diaz et al. | |
| 2005/0256579 A1* | 11/2005 | Keller | A61F 2/4425 623/17.15 |
| 2006/0030943 A1 | 2/2006 | Peterman | |
| 2006/0200134 A1 | 9/2006 | Freid et al. | |
| 2010/0211176 A1* | 8/2010 | Greenhalgh | A61F 2/447 623/17.15 |
| 2011/0153020 A1 | 6/2011 | Abdelgany et al. | |
| 2012/0016480 A1 | 1/2012 | Gerber et al. | |
| 2012/0083846 A1 | 4/2012 | Wallenstein et al. | |
| 2012/0203284 A1 | 8/2012 | Khanna | |
| 2012/0283782 A1 | 11/2012 | Ryan et al. | |
| 2014/0114420 A1 | 4/2014 | Robinson | |

OTHER PUBLICATIONS

European Supplementary Search Report for European Patent Application No. 15863794.2 dated Jun. 15, 2018.
Chinese National Phase Entry Search Report for Chinese Patent Application No. 2015899699201 dated Jul. 30, 2018.

* cited by examiner

ANGULATING BONE PLATE

CROSS-REFERENCE TO RELATED APPLICATION(S)

The present application claims priority benefit to a provisional patent application which is entitled "Angulating Bone Plate," which was filed on Nov. 24, 2014, and assigned Ser. No. 62/083,763. The entire content of the foregoing provisional patent application is incorporated herein by reference.

BACKGROUND

Technical Field

The present disclosure relates to devices and systems for fixation and/or support of bones. In particular, the present disclosure relates to a spinal plate assembly for fixation and/or support of bones of the spinal column. The plate of the present disclosure has particular application in situations where the surgical goal is to fuse one or more spinal levels.

Background Art

Spinal plates are commonly used and there are many versions in the prior art. Prior art spinal plates generally consist of one or more structural elements that are connected to each of the vertebral bodies adjacent to the level(s) to be fused via screws passing through holes in the structural elements and into the vertebral bodies. Some type of locking mechanism is generally provided to prevent or resist screw migration back through the structural elements. Spinal plates can be used for fusions throughout the spine.

In some instances, there may be a benefit to adjust the lordosis of the segment. One way to achieve that adjustment is via an adjustable interbody fusion device, such as that described by U.S. Pat. No. 8,007,536 to Christensen. The contents of the Christensen '536 patent are incorporated herein by reference. When adjusting the lordosis of the interbody device, there may also be a benefit to have a similar adjustment in the spinal plates.

The present disclosure relates to spinal plates that accommodate a range of lordosis and then can be locked in a selected lordosis position.

SUMMARY

According to the present disclosure, an advantageous spinal plate is provided. Exemplary spinal plates according to the present disclosure generally include two inter-related structural elements. In an assembled position, the two elements mate to form a plate. In combination, the plate has mounting features, e.g., at least two holes to permit bone screws or other fasteners to penetrate the structural elements and engage vertebral bodies, e.g., adjacent to the disc to be fused. In general, the two elements are permitted to move relative to each other unless and until a locking feature is engaged, which locks the two elements relative to each other. The locking feature is generally releasable, i.e., it is possible to "reverse" the locking function if desired.

The present disclosure further provides an implant assembly that includes an angulating bone plate and associated first/second intervertebral plates that extend therefrom. The angulating bone plate generally includes an interleaved elements, e.g., an upstanding tab that cooperates with opposing faces of an opening, that permit rotational movement as between first/second implant elements until a desired relative orientation is achieved. At such time, a fixation/locking element is generally employed to fix the first/second implant elements relative to each other. The rotational movement permitted is generally in multiple planes based on the cooperative arcuate surfaces provided in the disclosed elements, i.e., side-to-side and top-to-bottom freedoms of movement.

Additional features, functions and advantages associated with the disclosed spinal plate will be apparent from the detailed description which follows, particularly when read in conjunction with the appended figures.

BRIEF DESCRIPTION OF DRAWINGS

To assist those of skill in the art in better understanding how to make and use the disclosed spinal plate, reference is made to the accompanying figures, wherein.

DESCRIPTION OF EXEMPLARY EMBODIMENT(S)

Figure 1:
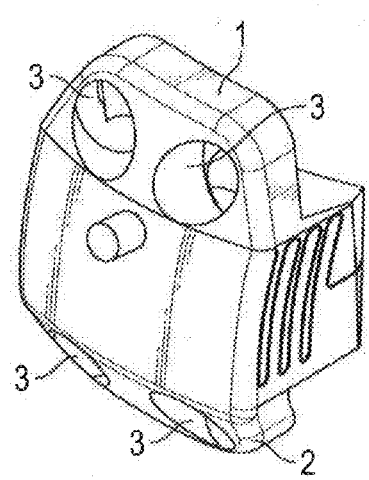
FIG. 1 is an oblique view of an exemplary spinal plate according to the present disclosure.

In exemplary embodiments of the present disclosure, an advantageous spinal plate is provided. With initial reference to FIGS. 1-7, exemplary spinal plates according to the present disclosure include two inter-related structural elements. In an assembled position (FIG. 1), the two elements (1,2) mate to form a plate. In combination, the plate has at least two holes (3) to permit bone screws or other fasteners to penetrate the structural elements and engage vertebral bodies, e.g., adjacent to the disc to be fused. In general, the two elements are permitted to move relative to each other unless and until a locking feature is engaged, which locks the two elements relative to each other. The locking feature is generally detachable or reversible, such that the two elements may be allowed to again move relative to each other, as may be desirable in a clinical application, and then re-locked relative to each other (on multiple occasions).

For clarity of description, the two elements are referenced as "top" and "bottom"—these designations reference relative positioning of the two elements based on a patient's spinal anatomy, but it is to be understood that the "top" element could be the "bottom" element (and vice versa) without departing from the spirit or scope of the present disclosure. Similarly, in different anatomical applications, the top/bottom relationship may instead be a side-to-side relationship, as will be apparent to persons skilled in the art.

Figure 2:
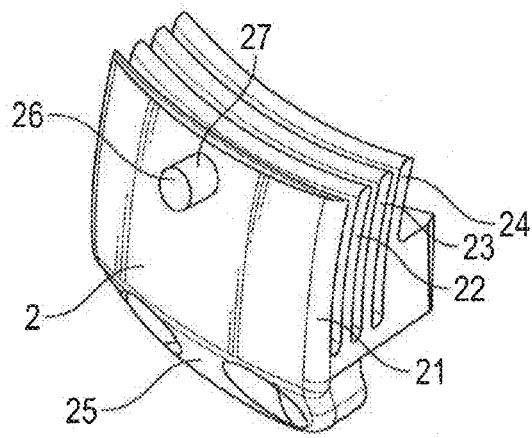
FIG. 2 is an oblique view of an exemplary bottom element of the disclosed spinal plate.
Figure 3:
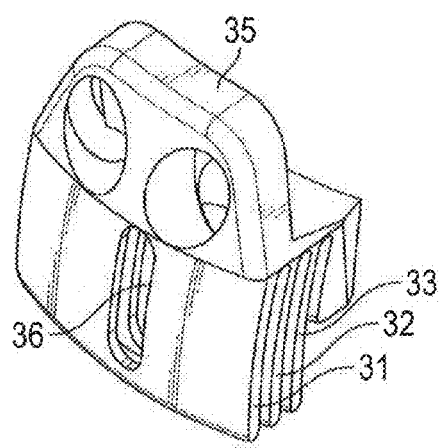
FIG. 3 is an oblique view of an exemplary top element of the disclosed spinal plate.

As shown in FIGS. 2 and 3 (showing respectively exemplary bottom and top elements), the mating is via a series of interacting sheets (21, 22, 23, 24, 31, 32, 33) that extend towards each other from the screw receiving portions of the elements (25, 35). The sheets of the bottom element (21, 22, 23, 24) may be aligned with spacings or channels defined between the sheets of the top element (31, 32, 33) to enable mating and sliding of the top element relative to the bottom element. Each sheet defines a generally planar or arcuate geometry that further defines two generally opposing faces. When mated, one or more "bottom sheets", e.g., sheet 22, is sandwiched between and is in confronting relation with opposed faces of two "top sheets", e.g., sheets 31, 32. Similarly, one or more "top sheets", e.g., sheet 32, is positioned between and is in confronting relation with opposed faces of two "bottom sheets", e.g., sheets 22, 23. Thus, mating of elements 1, 2 generally involves an interleaving of cooperative sheets associated therewith. However, it is to be noted that a single interleaving of sheets may be effective to achieve the desired clinical results of the present disclosure, in which case a single sheet is positioned between and is in confronting relation with opposed faces of two other sheets.

Figure 4:
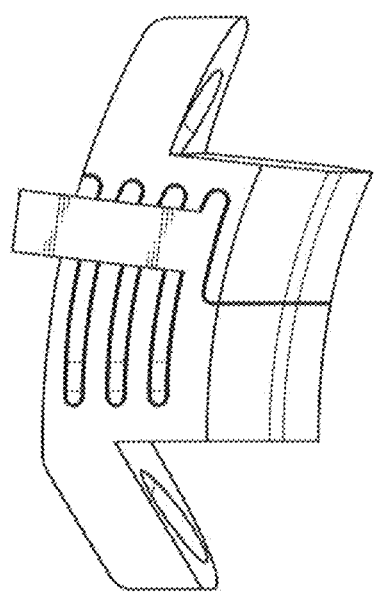
FIG. 4 is a right section view of an exemplary spinal plate according to the present disclosure.
Figure 5:
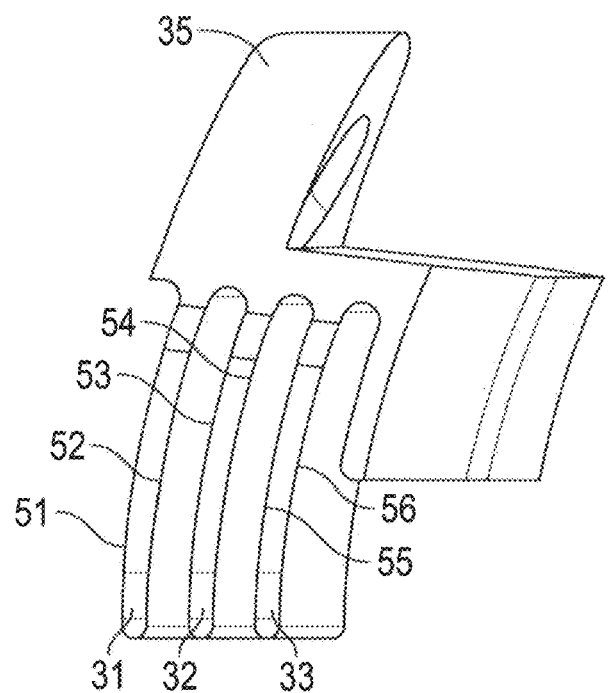
FIG. 5 is a right section view of an exemplary top element of the disclosed spinal plate.
Figure 6:
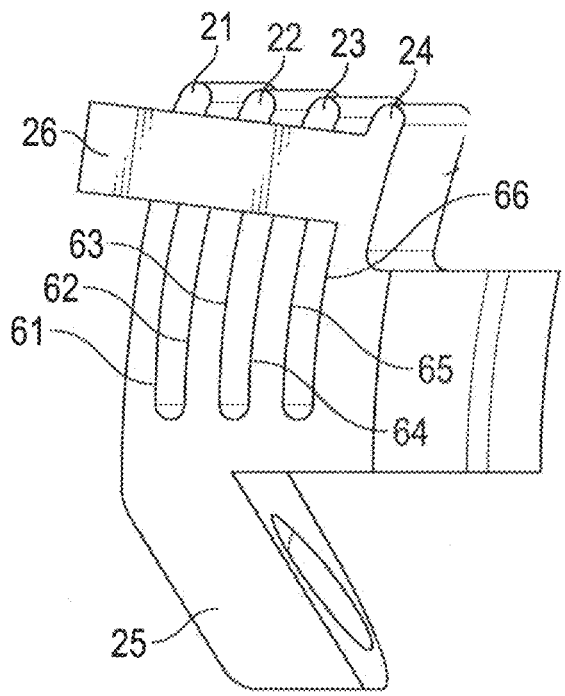
FIG. 6 is right section view of an exemplary bottom element of the disclosed spinal plate.

As shown in FIGS. 4-6, it is preferable that all of the sheets (21, 22, 23, 24, 31, 32, 33) have faces that are or are defined by (in whole or in part) arcs (51, 52, 53, 54, 55, 56, 61, 62, 63, 64, 65, 66) sharing a common center. This arcuate geometry ensures that the relative movement of one element (1) to the other element (2) is consistent with a rotation about the common center. This "rotational" movement of the first element relative to the second element is to be contrasted with "planar translation" (i.e., side-by-side linear translation), and such "rotational" movement advantageously facilitates spinal alignment during clinical procedures. Thereafter, once locked in place, the disclosed bone plate—in combination with an implant—is effective to establish a desired spinal alignment.

When the disclosed plate is created in a configuration as described above and applied to the anterior aspect of a spinal segment (i.e., vertebral body, disc, vertebral body) via screws or other fasteners, movement of one element relative to the other will allow a flexion/extension movement of the spine, without significant distraction or compression of the spinal segment. This relative movement of the elements (1, 2) may be beneficial in enabling proper alignment of the spine for the fusion procedure, which has been shown to be beneficial to outcomes.

To provide stability to a treated segment, the two elements (1, 2) must be locked relative to each other. In exemplary embodiments of the present disclosure, the means to lock the two elements together is enabled by features structurally associated with both elements. As shown in FIG. 2, an exemplary locking feature includes a fastener (26) that extends in a generally front to back direction relative to the bottom element (2). As shown in FIG. 6, the fastener is connected to, or an integral part of, the back-most sheet (24). Each of the sheets closer to the front (21, 22, 23) have aligned holes to permit the fastener to pass through.

On the top element (1), each of the exemplary sheets (31, 32, 33) has a slot 36. The slot enables the fastener (26) to pass through the sheet, even when the top element (1) is shifted relative to the bottom element (2).

To lock the top element (1) relative to the bottom element (2), a nut (not shown) or functionally similar structure is applied to the front-most aspect (27) of the fastener (26). In implementations that use a nut, the fastener (26) is generally threaded along at least the front-most aspect (27) of its length. A variety of other fasteners could be used according to the present disclosure, including clamps, clips, pins, or similar fastening structures. As the fastener is tightened, a compressive force is applied across each of the sheets. Using a structural material, such as stainless steel or a commonly used medical implant material, such as a titanium alloy, a significant friction force is generated at each face of each sheet. The plate could also be fabricated (in whole or in part) using structural plastics, such as PEEK or UHMWPE, but these polymeric materials are less preferred as they tend to have lower coefficients of frictions when coupled with themselves than the metals commonly used in medical implants.

By having multiple sheets, the frictional force, which maintains the position of the two elements (1, 2) when locked, is also multiplied, providing greater stability. For this reason, there may be advantages to have a greater number of sheets for the given dimensions of the plate, although effective results are achievable with fewer sheets. Indeed, there can be as few as one sheet extending from the top element, and as few as two sheets extending from the bottom element (or vice versa), but a greater number of inter-leaved sheets may be preferred (assuming clinical space to accommodate the plate's dimension) for the stability/frictional force attributes noted above.

Figure 7:
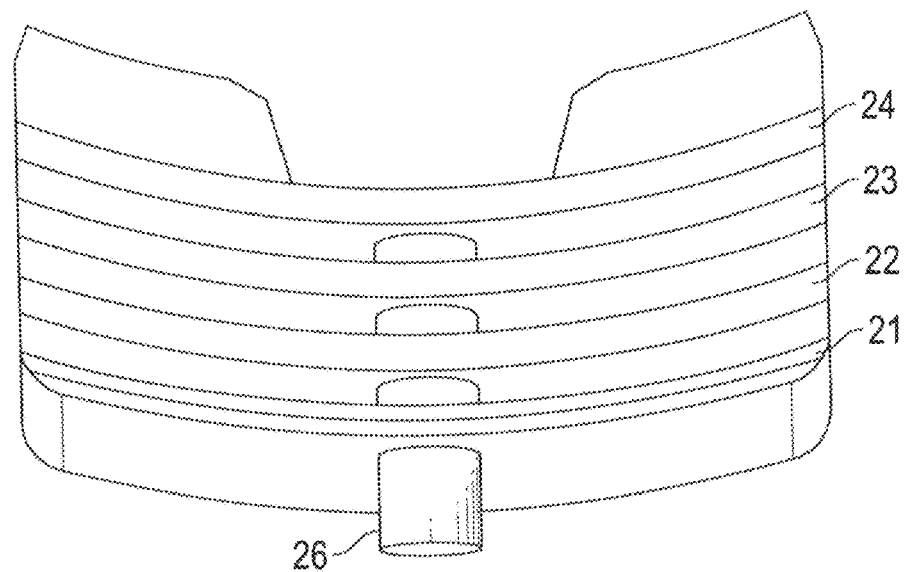
FIG. 7 is a top view of an exemplary bottom element of the disclosed spinal plate.

As described above, the sheets are generally curved in at least one plane, as shown in FIGS. 4-6. In the plane perpendicular to the arcs (51, 52, 53, 54, 55, 56, 61, 62, 63, 64, 65, 66), the sheets may be flat or curved. FIG. 7 shows the sheets curved in the perpendicular plane. The benefit of this configuration is that it imparts greater bending stiffness to each of the individual sheets and also resists translations and rotations of the top element with respect to the bottom element in directions other than intended.

When the angulating bone plate of the present disclosure is coupled with a disc implant, such as a disc implant of the type described by Christensen in U.S. Pat. No. 8,007,536, a surgical procedure can be described where the segment lordosis is adjusted intraoperatively, and then fixed in a particular location.

The surgical procedure would generally be performed as follows:
1. The disc space is approached in a standard fashion (e.g., anteriorly, laterally or posteriorly, as well as the intermediate positions, such as TLIF or transforaminal).
2. The disc is partially evacuated in the standard fashion.
3. The endplates are prepared in the standard fashion, removing the cartilage.
4. A trial implant is placed in the disc space to determine the appropriately sized implant.
5. An implant, e.g., an implant of the type described by Christensen in U.S. Pat. No. 8,007,536, is implanted in the disc space.
6. A plate fabricated according to the current disclosure is applied adjacent to the implant.

7. The spinal segment is positioned to set the correct amount of lordosis. This can be done in a variety of means, including moving portions of the table that the patient is resting on, or placing additional padding in certain locations between the patient and the bed, or by other means such as an inflatable balloon placed between the patient and the bed prior to surgery, and then partially inflated during surgery to induce the correct amount of lordosis.

8. Once the lordosis is satisfactory, the plate of the current disclosure is locked in position using the fastener/fastening mechanism.

Of note, the positioning/locking steps can be repeated, if desired, i.e., by first releasing the fastener/fastening mechanism, resetting the amount of lordosis, and then re-locking the disclosed plate to fix the adjusted amount of lordosis.

Alternatively, a plate of the current disclosure may be fabricated with a geometry that is adapted to engage the implant, e.g., an implant of the typed disclosed by Christensen in U.S. Pat. No. 8,007,536, so that the plate and implant can be pre-assembled and applied in a single step, as opposed to two steps (i.e., steps 5 and 6 above).

Figure 8:
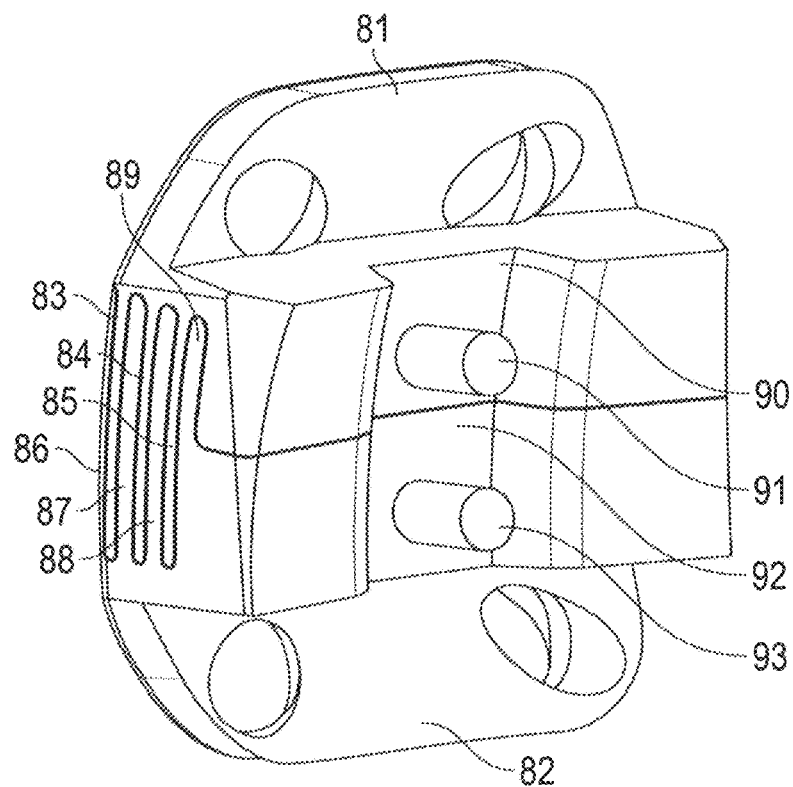
FIG. 8 is an oblique back view of an alternate exemplary embodiment of the disclosed spinal plate.

FIG. 8 shows an alternate exemplary embodiment of the present disclosure. In the alternative embodiment of FIG. 8, the plate is fabricated with a geometry that is adapted to engage an implant. In particular, FIG. 8 shows a top element (81) and a bottom element (82). Sheets of the top element (83, 84, 85) and sheets of the bottom element (86, 87, 88, 89) are shown in a fully aligned/interleaved position. Towards the back of the assembled spinal plate, there may be one or more features that facilitate engagement with an implant.

As shown in FIG. 8, the exemplary embodiment includes both surfaces and fasteners that facilitate engagement with an implant. For example, surfaces 90 and 92 of the top and bottom elements, respectively, may be advantageously shaped to engage the front of the implant. Likewise, depending on the design of the implant, one or more fasteners (91, 93) may be provided as a means to connect the disclosed plate relative to an implant. A variety of fasteners could be used for this purpose, including threaded connectors, as well as a variety of clamps, clips, pins or similar fastening structures.

It is generally preferable that both the top element (81) and the bottom element (82) include faces at the extreme back of the plate, such that both the top and bottom elements are adapted to engage different components of an implant. This design feature enables both insertion of the assembled plate and implant, and an ability to manipulate both the plate and the implant simultaneously when adjusting rotation in situ (e.g., by extending or collapsing the top and bottom elements relative to each other).

Figure 9:
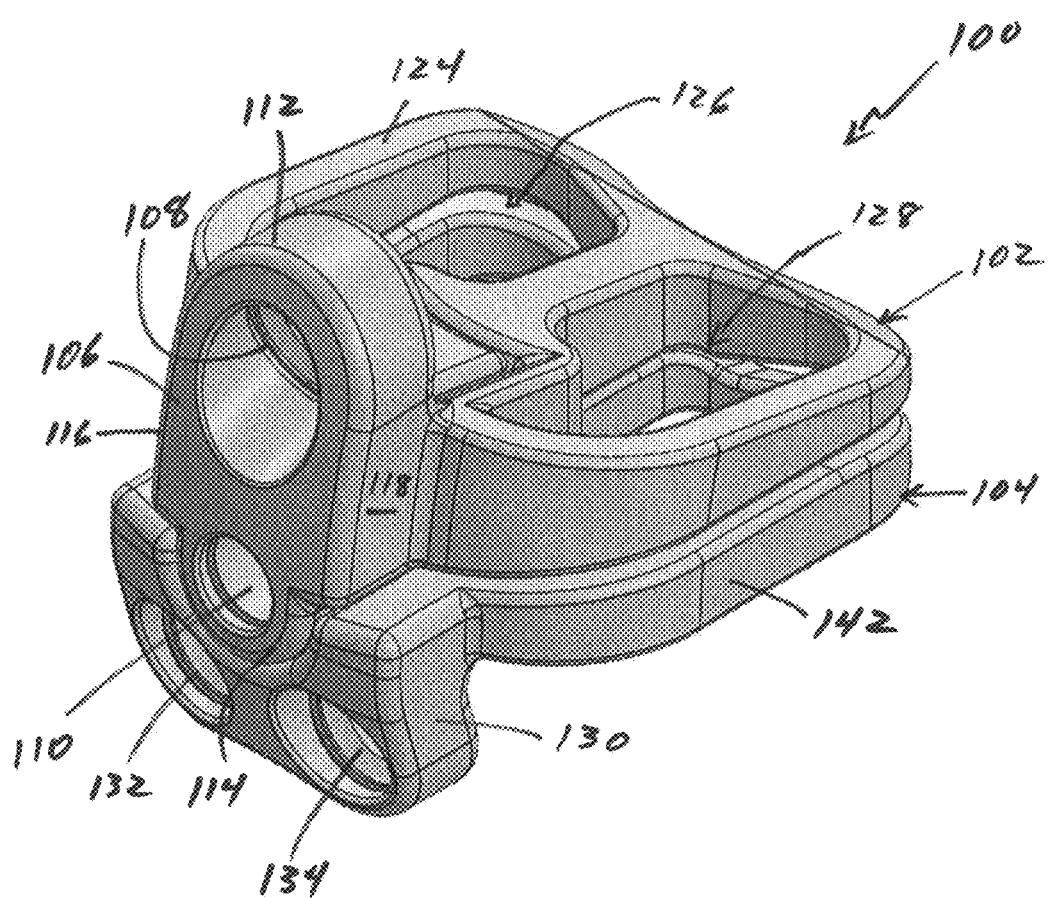
FIG. 9 is an oblique view of an exemplary bone plate and inter-body device in an assembled configuration according to the present disclosure.
Figure 10:
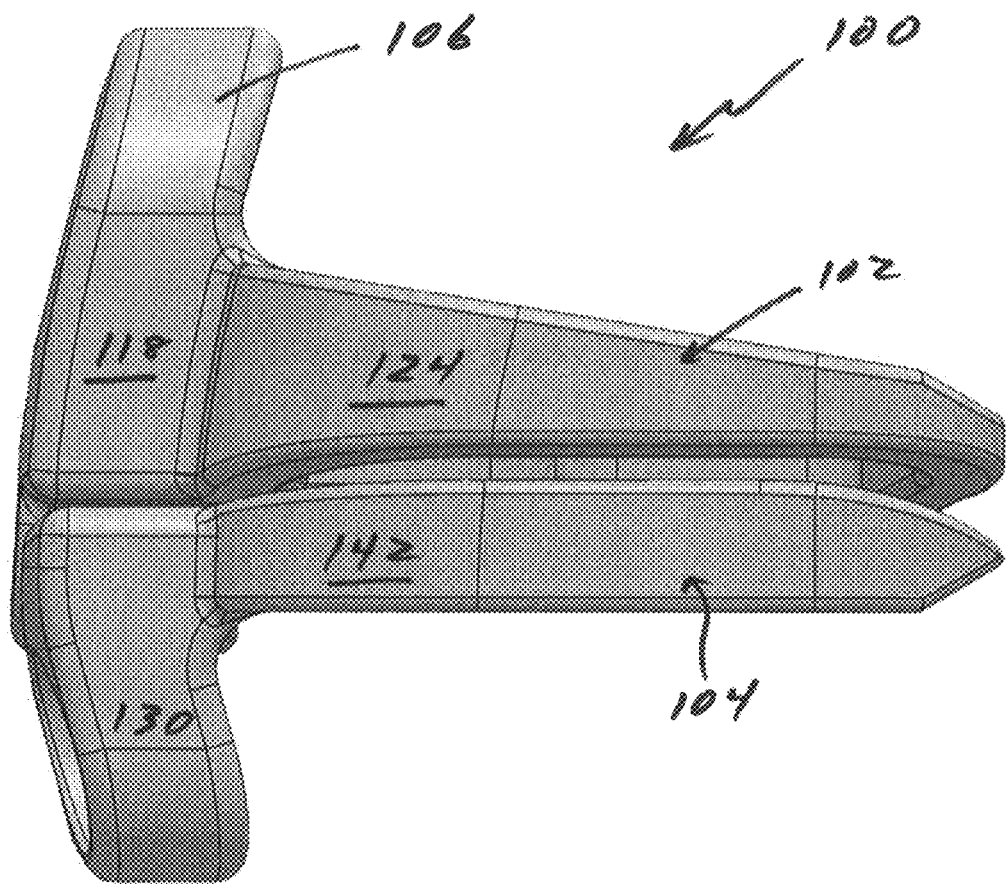
FIG. 10 is a side view of the assembled, exemplary bone plate and inter-body device shown in FIG. 9.
Figure 13:
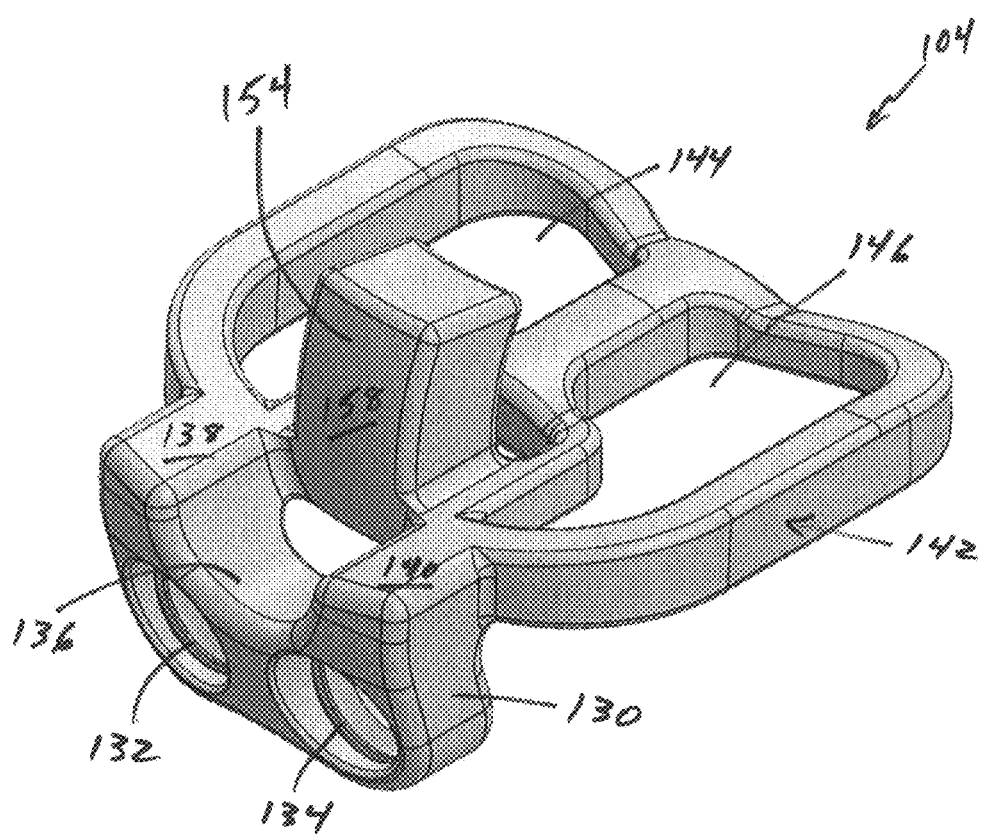
FIG. 13 is an oblique view of an exemplary inferior implant element that may be assembled with a superior implant element to define a bone plate and inter-body device according to the present disclosure.
Figure 14:
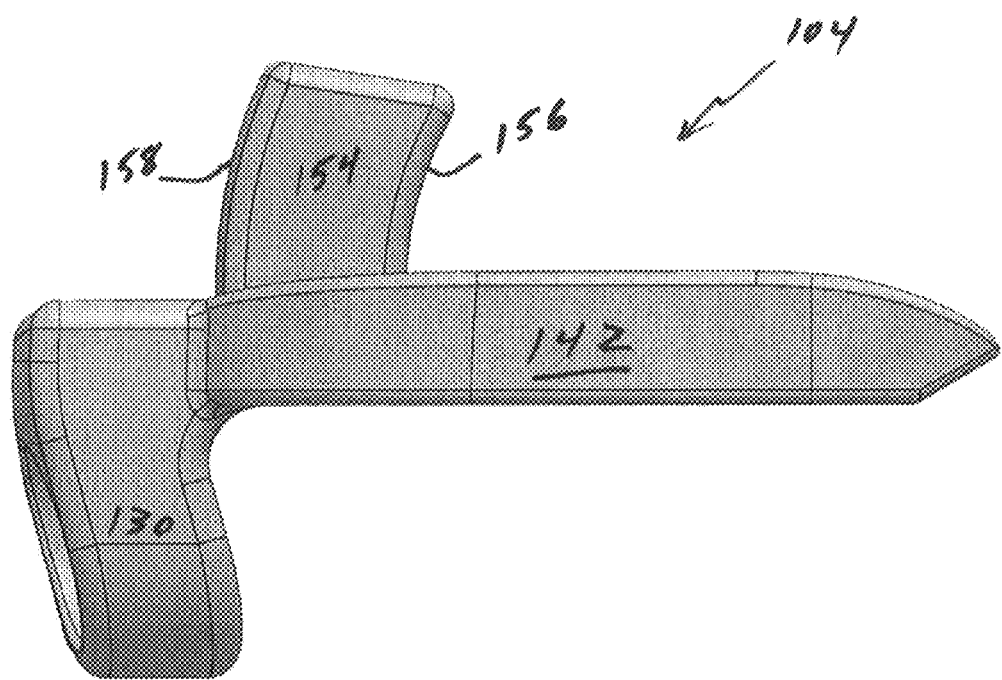
FIG. 14 is a side view of the exemplary inferior implant element shown in FIG. 13.
Figure 15:
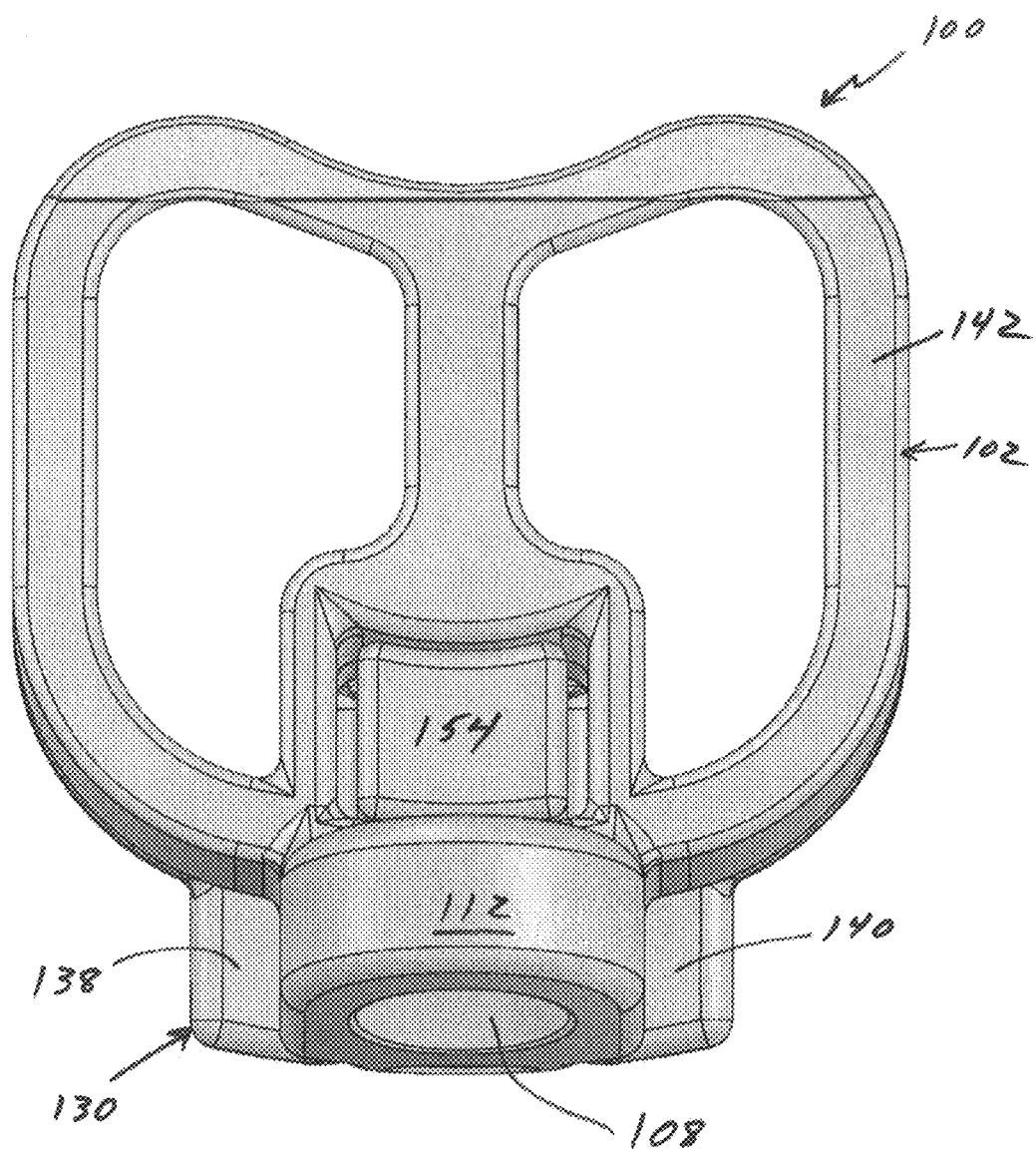
FIG. 15 is a top view of the assembled, exemplary bone plate and inter-body device of FIGS. 8-14.

Turning to FIGS. 9-15, a further exemplary implementation of the present disclosure is depicted and described herein. Specifically, FIGS. 9, 10 and 15 show an exemplary bone plate and inter-body device 100 that includes a superior implant element 102 (FIGS. 11 and 12) and an inferior implant element 104 (FIGS. 13 and 14). The bone plate and inter-body device 100—referenced as "implant assembly 100" hereafter—provides first/second elements that integrally combine the structures associated with an angulating bone plate and the structures associated with an inter-body device or implant. The inter-body device/implant aspects of the disclosed implant assembly 100 may be advantageously based on the teachings of U.S. Pat. No. 8,906,095 to Christensen et al., the content of which is incorporated herein by reference in its entirety.

Of note, the terms "inferior" and "superior" are used for convenience of description. However, it is to be understood throughout this disclosure that the "inferior implant element" may be positioned inferior or superior to the "superior implant element", and that the "superior implant element" may be positioned inferior or superior to the "inferior implant element". Thus, the terms "inferior" and "superior" are equivalent to "first" and "second" implant elements for purposes of implementation of the present disclosure, i.e., the features/functions may be implemented interchangeably according to the present disclosure.

As shown in FIGS. 9-15, the superior implant element 102 includes an upstanding flange 106 that defines a first hole 108 for use in mounting superior implant element 102 relative to vertebral bodies, e.g., using a bone screw or other fastener (not shown), and a second hole/opening 110 that facilitates fixation/locking of superior implant element 102 relative to inferior implant element 104. The interior of hole/opening 110 may be advantageously threaded to facilitate the noted fixation/locking functionality using a threaded screw/fastener (not shown). In addition, threading of the interior of hole/opening 110 permits withdrawal of a threaded screw/fastener advanced therethrough, thereby permitting "unlocking" of superior implant element 102/inferior implant element 104, as may be clinically desired in connection with positioning/implantation of implant assembly 100.

Upstanding flange 106 generally defines an arcuate/semi-circular top face 112 and an arcuate/semi-circular bottom face 114. The arcuate/semi-circular bottom face 114 is generally inwardly stepped relative to the side faces 116, 118 of upstanding flange 106, thereby defining first and second ledge faces 120, 122 on either side of arcuate/semi-circular bottom face 114.

First and second ledge faces 120, 122 are adapted to engage opposed regions of inferior implant element 104 (see FIG. 9), while the arcuate/semi-circular bottom face 114 extends into and cooperates with a corresponding arcuate/semi-circular recess defined by interior implant element 104 (as described below). A first intervertebral element 124 extends from upstanding flange 106 and defines first and second openings 126, 128. Features and functions of first intervertebral element 124 are described in greater detail below and with reference to U.S. Pat. No. 8,906,095, previously incorporated herein by reference.

Turning to the inferior implant element 104, it is noted that such element includes a flange portion 130 that defines a pair of spaced holes/openings 132, 134 for use in fixing the inferior implant element 104 relative to vertebral bodies, e.g., using bone screws or other fasteners (not shown). Flange portion 130 also defines an arcuate/semi-circular recess 136 (best seen in FIG. 13) that is configured to receive and cooperate with arcuate/semi-circular bottom face 114 of superior implant element 102. The interacting arcuate faces of upstanding flange 106 and flange portion 130 permit rotational motion as between the superior and inferior implant elements 102, 104. The degree of rotational motion is limited by the abutting interaction of first and second ledge faces 120, 122 defined by upstanding flange 106 and the opposed upper faces 138, 140 defined on either side of arcuate/semi-circular recess 136 of flange portion 130. The geometries of the ledge faces 120, 122 and upper faces 138, 140 may be formed so as to accommodate a desired level of rotational freedom between first and second implant elements 102, 104, as will be apparent to persons skilled in the art based on the disclosure herein. Of note, the ledge faces 120, 122 and the upper faces 138, 140 can be used with an extending instrument to induce lordosis of the segment. Indeed, clinical interaction with one or more of these surfaces/faces provides an alternate method for inducing lordosis (see step 7 in the surgical procedure outlined above).

A second intervertebral element 142 extends from flange portion 130 and defines first and second openings 144, 146. Features and functions of second intervertebral element 142 are described in greater detail below and with reference to U.S. Pat. No. 8,906,095, previously incorporated herein by reference.

The first and second openings associated with each of the first inter-vertebral element 124 and the second intervertebral element 142 encompass a substantial portion of the surface areas of the opposed faces thereof, e.g., greater than 50% of such surface areas. In this way, bone in-growth into implant assembly 100 so as to "fix" first and second intervertebral elements 124, 142 relative to each other is encouraged. However, it is to be understood that the present disclosure is not limited by or to implementations wherein the openings constitute openings at the noted level. For example, the openings may constitute a lesser percentage of the surface area, e.g., on the order of 10%, or an intermediate level, e.g., between 10% and 50%. Still further, the openings may constitute a greater percentage of the surface area, e.g., greater than 50%. It is further noted that bone in-growth may be achieved in exemplary embodiments without the provision of openings in the surface area, e.g., wherein fusion occurs through bone growth at least in part anterior to the first and second inter-vertebral elements.

Figure 11:
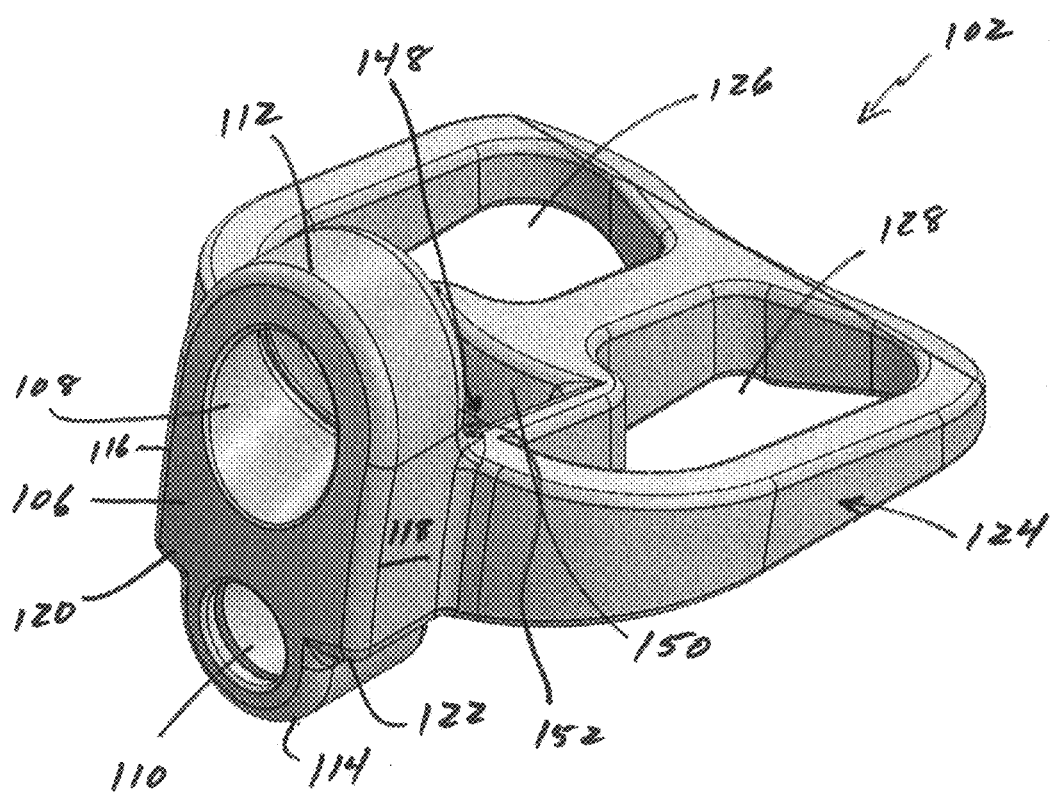
FIG. 11 is an oblique view of an exemplary superior implant element that may be assembled with an inferior implant element to define a bone plate and inter-body device according to the present disclosure.
Figure 12:
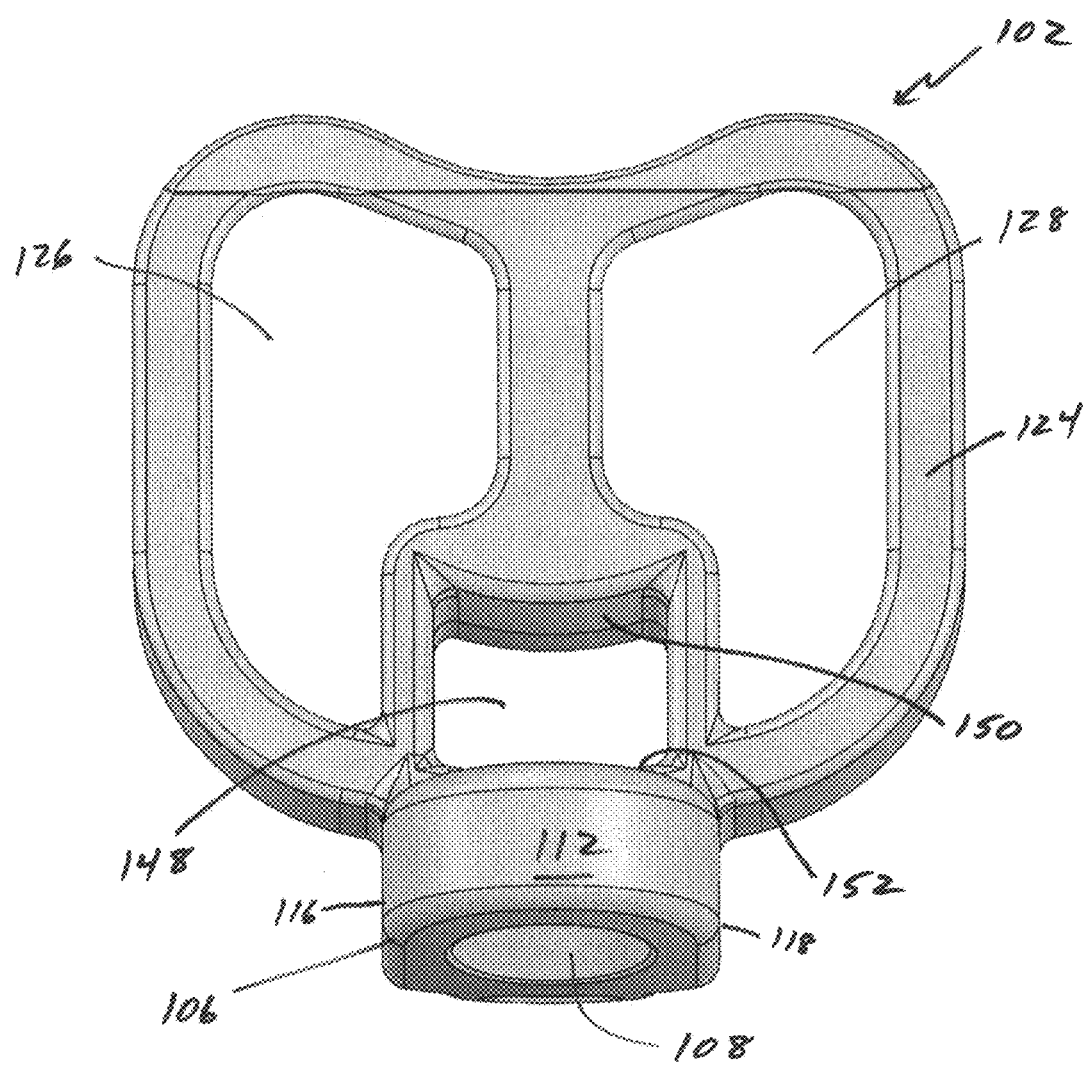
FIG. 12 is a top view of the exemplary superior implant element shown in FIG. 11.

With reference to FIG. 11, superior implant element 102 defines a bounded opening 148 that is nested between the first and second openings 126, 128 of the first intervertebral element 124 and substantially centered on the central axis of the first intervertebral element 124. A first boundary wall 150 of bounded opening 148 defines an arcuate surface and functions as a first "sheet" for purposes of interleaved interaction of superior and inferior implant elements 102, 104, according to the present disclosure. The opposed boundary wall 152 may be defined by or in proximity to an interior face of the upstanding flange 106, and such opposed boundary wall 152 functions as a second "sheet" for purposes of interleaved interaction of superior and inferior implant elements 102, 104, according to the present disclosure.

Turning to FIGS. 13 and 14, the inferior implant element 104 defines an upstanding tab 154 that is configured and dimensioned to pass into bounded opening 148 of the superior implant element 102. Upstanding tab 154 defines arcuate opposed faces 156, 158 that cooperate with corresponding radiused boundary walls 150, 152 of bounded opening 148 to permit limited axial rotational movement as between superior and inferior implant elements 102, 104. Thus, upstanding tab 154 functions as a further "sheet" according to the present disclosure, the upstanding tab 154 being configured and dimensioned to be interleaved between opposed sheets defined by the superior implant element 102, i.e., boundary walls 150, 152 thereof.

As shown in FIG. 14, upstanding tab 154 defines arcuate surfaces 156, 158. This further radiused geometry associated with upstanding tab 154 and the opposed boundary walls 150, 152 of the superior implant element 102 permits a further rotational degree of freedom as between the superior and inferior implant elements 102, 104. In particular, repositioning of the superior and inferior elements 102, 104 is possible based on flexion/extension rotational freedom of movement which are accommodated by the interleaved upstanding tab 154 and cooperating boundary walls 150, 152. A small amount of lateral bending rotation, i.e., rotation about an anterior-to-posterior axis, may also be accommodated thereby.

Once the desired relative positioning of superior and inferior implant elements 102, 104 is achieved clinically, the implant elements 102, 104 may be fixed/locked relative to each other by advancing a locking element (not pictured) through threaded hole/opening 110 to engage face 158 of upstanding tab 154. Repositioning is permitted by reversing the direction of the locking element to disengage from face 158, and then retightening once the desired relative orientation is achieved.

With further reference to FIG. 14, it is noted that flange portion 130 defines an angled/arcuate downward extension relative to a horizontal plane defined by second intervertebral element 142. This angled/arcuate geometry facilitates positioning of the inferior implant device 104 relative to surrounding anatomical structures.

As described in greater detail in U.S. Pat. No. 8,906,095 (incorporated herein by reference), the outer profiles of the first and second inter-vertebral elements 124, 142 are the same (or substantially the same) such that, when coupled/assembled, a substantially uniform outer edge/profile is defined. Thus, the combined/assembled profiles of the first and second inter-vertebral elements of implant assembly 100 define an anterior edge and a posterior edge. The anterior edge may be broken into three (3) sub-regions for description purposes: two anterolateral edges that surround a central anterior edge. Recessed geometry associated with anterolateral edges relative to the central edge may allow placement of bone materials and/or other desired materials anterior to implant assembly 100 in a location that may facilitate and/or induce bone fusion. This recessed region adjacent the anterolateral edges may also advantageously accommodate placement/coupling of fusion blocks. The outer profiles of the first and second inter-vertebral elements 124, 142 may also be broken into two regions, where the plate portion (106) is not central, but is instead anterolateral, with the remainder of the anterior edge recessed.

With reference to the coupling of exemplary implant assembly 100, it is noted that the first and second inter-vertebral elements 124, 142 define cooperative inner faces that facilitate relative movement therebetween for an initial period of time post-implantation of implant assembly 100. Thus, the inner face of first intervertebral element 124 defines a central region and two wing regions. The central region and wing region together form or bound opening 126, whereas the central region and the other wing region form or bound opening 128.

The inner face of second intervertebral element 142 also defines a central region and two wing regions. The central region and first wing region together form or bound opening 144, whereas the central region and the other wing region form or bound opening 146.

The first and second inter-vertebral elements 124, 142 of implant assembly 100 are advantageously movably coupled with respect to each other when the inner face of first inter-vertebral element 124 is brought into abutting engagement with the inner face of second inter-vertebral element 142. When brought into the noted abutting engagement, opening 126 of first inter-vertebral element 124 substantially aligns with opening 144 of second inter-vertebral element 142, and opening 128 of first inter-vertebral element 124 substantially aligns with opening 146 of second inter-vertebral element 142. Still further, the central region of first inter-vertebral element 124 is in abutting relationship with the central region of second inter-vertebral element 142 to define an articulating region therebetween (see FIG. 6 of U.S. Pat. No. 8,906,095, incorporated herein by reference).

Generally, the articulating region provides primary contact between the first and second inter-vertebral elements 124, 142. The openings 126, 128 formed in wing regions of the first inter-vertebral element 124 and the openings 144, 146 formed in wing regions of the second inter-vertebral element 142 may receive bone materials (or other materials) to facilitate bone in-growth therethrough. In addition, interaction/contact between the respective wing regions of the first and second inter-vertebral elements 124, 142 advantageously function to limit lateral bending therebetween. In exemplary embodiments of the present disclosure, implant assembly 100 is symmetric (or substantially symmetric) about an anterior-posterior plane, i.e., along the plane defined by the articulating region.

The central region of the first inter-vertebral element 124 is generally defined as a swept surface with a first profile in the medial lateral direction and a second profile in the anterior-posterior direction. It is generally preferable that the first profile in the medial-lateral direction be a single arc. It is also generally preferable that the profile in the anterior-posterior direction be composed of a line with an arc, wherein the line is tangent to the arc and arc is posterior. This arc combination advantageously allows for normal anatomical motion of a patient in flexion-extension, while controlling contact forces between the first and second inter-vertebral elements 124, 142. However, the present disclosure is not limited by or to the arc-based implementations described herein.

The central region of the second inter-vertebral element 142 is also generally defined as a swept surface with a first profile in the medial lateral direction and a second profile in the anterior posterior direction. It is generally preferable that the first profile be a single arc. It is also generally preferable that the second profile be composed of a line. However, as with the first inter-vertebral element 124, the present disclosure is not limited by or to the arc-based implementations described herein.

So as to reduce contact stresses, it is generally preferable that the radii of the mating arcs in the medial lateral direction be of similar (but not the same) value, thereby reducing the contact stress between the first and second inter-vertebral elements 124, 142. Also, the extent of the profile of the first inter-vertebral element 124 is generally greater than the second inter-vertebral element 142 to enable/facilitate rotation of the second inter-vertebral element 142 relative to the first inter-vertebral element 124.

There is also an advantageous relationship between the profiles in the anterior-posterior direction of exemplary first and second inter-vertebral elements 124, 142 of the present disclosure. For example, the anterior-posterior profile of the first inter-vertebral element 124 is typically matched with the anterior-posterior profile of the second inter-vertebral element 142. This matching of anterior-posterior profiles enables the necessary and/or desired flexion-extension motion of a patient and facilitates positional adaptability of the disclosed disc implant in an initial period post-implantation. Of note, the central regions of first and second inter-vertebral elements 124, 142 define a contact region in the aligned position. It is also noted that as between the medial-lateral profiles and the anterior-posterior profiles, the anterior-posterior curves are generally not as closely matched.

While exemplary profiles have been described with reference to implant assembly 100, a variety of alternate profiles are contemplated. For example, medial lateral profiles may be formed/defined by geometries that include radiused opposing faces, elliptical opposing faces, spline-shaped opposing faces or other generally curved elements. Similarly, the anterior-posterior profiles may be formed/defined by geometries that include radiused opposing faces, elliptical opposing faces, spline-shaped opposing faces or other generally curved elements. It is further contemplated that the articulating geometries may be reversed/inverted, such that the disclosed geometric features and functions of the first inter-vertebral element 124 described herein may be associated instead with second inter-vertebral element 142, and vice versa. Thus, the geometric features/functions of profiles may be traded. However, it is noted that a reversal of the profile features described herein may not be preferable because the center of rotation of the first and second inter-vertebral elements 124, 142 would be potentially shifted away from the natural center of rotation of the spine segment, which is believed to be in the posterior half of the lower body of the spine segment. Also, there is a benefit of a relationship (alignment) between interbody and plate. That is, the centers of the radii defining the sheets of the plate should be positioned appropriately relative to the anterior-posterior profiles.

As described herein, exemplary disc implant assemblies according to the present disclosure are adapted for clinical insertion between vertebrate bodies. The implant generally comprises two elements, which are coupled together forming the disc implant. The opposing surfaces of the two elements are described as internal coupling surfaces and may include features/cooperative mechanisms that advantageously function to movably couple the elements relative to each other upon initial implantation of the disclosed spinal implant. Thus, the coupling means/mechanism may serve to connect and/or align the first and second inter vertebral elements relative to each other. Coupling of the inter-vertebral elements may regulate movement of the first and second inter-vertebral elements relative to each other, i.e., prior to fixation of the first and second inter-vertebral elements relative to each other based on bone in-growth. Thus, coupling of the two inter-vertebral elements does not fixedly position the elements relative to each other. Minor movements of the elements relative to each other in at least one direction are generally permitted when said elements are coupled according to the present disclosure.

A third element may be advantageously positioned between the first and second elements described herein. Thus, for example, a non-metal component may be positioned between the first and second elements so as to be positioned between contact regions thereof. The non-metal component may be fabricated from a polymeric material, e.g., polyethylene, polyether ketone ketone (PEKK) and/or polyether ether ketone (PEEK). The non-metal component may take the form of a sheet, relatively thin block or surface treatment, and advantageously functions to prevent metal-to-metal contact, thereby reducing the potential for metal failure. Indeed, a sheet and/or block of the disclosed polymeric material may function as a wedge-like structure when introduced between the first and second elements in situ. In exemplary embodiments, the disclosed polymeric material may be positioned and/or applied to the "male" portion(s) of the first and/or second elements of the disclosed inter-vertebral elements.

As described herein, the disclosed spinal implant assemblies may also benefit from movability of the first and second inter-vertebral elements relative to each other that is achieved clinically based on the structural design and operation of the disclosed disc implant for a limited period of time. Exemplary disc implant assemblies of the present disclosure include a first inter-vertebral element having a first outer fusion surface and a first internal coupling surface, a second inter-vertebral element having a second outer fusion surface and a second internal coupling surface, a coupling means/mechanism for movably connecting/coupling the first and second inter vertebral elements relative to each other. In addition, each inter-vertebral element generally includes one or more osseointegrative sections enabling/facilitating further fixation of the first and second elements.

Overview information related to shape, coupling means/mechanisms, size, material, coating, coating material, osseointegrative section(s)/openings, incisions/circumferential inset regions, temporal movability and methods of treatment associated with advantageous spinal disc implant assemblies contemplated according to the present disclosure are described herein.

a. Shape

The disc implant according to the invention may have any shape that enables transient stabilization and stimulates long term fixation by fusion and bone in-growth.

The shape of the disc implant, as seen from the top, may include geometries such as a round, circular, oval, oblate or kidney shape. The disc implant may be designed for use in posterior or anterior surgery, but is preferably designed for use in anterior surgery, which may lead to a shorter recovery period after surgery. Alternatively, the disclosed implant may be designed for transforaminal lumbar interbody fusion or lateral lumbar interbody fusion.

b. Size

The circumference of the disc implant may be smaller than the circumference of the corpus. In particular, the geometry of the disclosed spinal disc implant may be defined such that the basis of the corpus protrudes relative to the implant at the front thereof. For example, the corpus may protrude at least 0.2 mm relative to the implant, and optionally by as much as 0.4 mm or 0.6 mm past the edge of the implant. In further exemplary embodiments of the present disclosure, the distance from the outer edge of the implant to the edge of the corpus is defined such that the distance is on the order of 5 mm or greater.

Such dimensional arrangement may advantageously provide and/or permit stimulation of bone growth at or along the side of the disc implant and, following fixation of the inter-vertebral elements relative to adjacent vertebral bodies, bone tissue may join at or along the outer edges of the disclosed inter-vertebral elements, thereby further fixing the inter-vertebral elements relative to each other after a period of time post-implantation.

c. Material

The disc implant assemblies according to the present invention may be fabricated from any material(s) suitable for implantation. Thus, the disclosed implant may be constructed from one or more materials selected from, but not limited to, the group of ceramics, polymers, bone and metals. Preferred are metals. polymers and ceramics. The material(s) may be in states of glassy, rubbery, semi-crystalline, or crystalline, before and/or after processing into the implant.

In exemplary embodiments of the present disclosure, the disclosed spinal implants may be constructed of metal or metal alloys selected from the group of, but not limited to, stainless steel, cobalt-chromium, titanium (Ti), titanium alloys, shape memory alloys, e.g., NiTi, tantalum (Ta), niobium (Nb), zirconium (Zr) and platinum (Pt). Preferred metals and metal alloys are titanium, tantalum, titanium alloys, and cobalt-chromium and alloys thereof. Exemplary cobalt-chromium materials for use according to the present disclosure include CoCrMo alloys. Exemplary titanium alloys for use according to the present disclosure include Ti6Al4V. Exemplary stainless steel materials for use according to the present disclosure include austenitic stainless steels, especially types 316 and 316L, and Ni-free stainless steel.

Metals, such as transition metals, may be used to fabricate disc implants according to the present disclosure. For example, tantalum (Ta)—a corrosion-resistant material—may be employed. Indeed, tantalum may be useful for implant fabrication according to the present disclosure because it is generally immune to the action of body liquids and is non-irritating. Titanium is a second transition metal that is corrosion resistant, offers high stiffness and is physiologically inert, thereby enhancing its usefulness according to the present disclosure. Titanium and tantalum have the unusual ability to osseointegrate. Furthermore, the anatomical position of disc implants fabricated from these metals may be easily analyzed by conventional imaging methods.

Exemplary ceramic materials for use according to the present disclosure include, but are not limited to, bio-inert ceramics (alumina ($Al_2O_3$), partially stabilized zirconia ($ZrO_2$), silicon nitride ($Si_3N_4$), bioactive ceramics (hydroxyapatite ($Ca_{10}(PO_4)_6(OH)_2$) and bioglasses), and resorbable ceramics (e.g., calcium phosphate ceramics such as tricalcium phosphate, $Ca_3(PO_4)_2$). Apatite refers to a group of phosphate minerals, usually referred to as hydroxylapatite, fluorapatite, and chlorapatite, named for high concentrations of OH—, F—, or Cl-ions, respectively, in the crystal lattice. Hydroxylapatite is the major component of tooth enamel and a large component of bone material. Hydroxylapatite is a naturally occurring form of calcium apatite with the formula $Ca_5(PO_4)_3(OH)$, but is usually written $Ca_{10}(PO_4)_6(OH)_2$ to denote that the crystal unit cell comprises two molecules. Hydroxylapaptite is easily accepted by the recipient and provides substantial stimulation of bone in-growth.

Most of the calcium phosphate ceramics are crystalline substances. The crystals are subjected to heat treatment at high temperatures, and sintered to produce a bioceramic material. Chemically, they are hydroxyapatite, tricalcium phosphate, or mixtures of the two. They are generally supplied as powders, granules, or porous or non-porous blocks.

Tricalcium phosphate is more porous than hydroxyapatite, and is biodegraded ten to twenty times faster. The sintering temperature also has an influence on the behavior of the finished product. Depending on manufacturing conditions, tricalcium phosphate will be totally resorbed within a few months, or take several years to be removed by bioresorption. In the body, it is partially converted to hydroxyapatite, which is biodegraded more slowly. In exemplary embodiments of the present disclosure, artificial bone material is employed, such as resorbable ceramic granules and resorbable tricalcium phosphate (TCP) ceramic granules.

The disclosed spinal implant may further be fabricated, in whole or in part, using glassy and pyrolytic carbon, which is highly efficient for stimulating bone fusion.

Exemplary polymers for use, in whole or in part, in fabricating spinal implants according to the present disclosure may be selected from, but are not limited to, the group of polylactides (PLA), polyglycolides (PGA), polyanhydrides, polyorthoesters, poly(D,L-lactic acid), poly(lactide-co-glycolide) (PLGA), poly-D,L-lactic acid-poly(ethylene glycol), polyphosphates, poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(methacrylic acid), ultra high molecular weight polyethylene (UHMWPE), polyether ether ketones (PEEK) and polyether ketone ketones (PEKK). Preferred polymers according to the present disclosure include PEEK and PEKK. According to exemplary embodiments, a polymeric element (e.g., sheet, block and/or surface treatment) may be positioned between opposing metallic surfaces according to the present disclosure.

Exemplary bone for use, in whole or in part, in fabricating spinal implants according to the present disclosure may be selected from the group of xenograft, allograft and autograft. Preferred bone according to the present disclosure include xenograft and allograft.

The disclosed implant may be fabricated from one or more suitable materials. Thus, in exemplary embodiments, the disclosed spinal implant is made of at least one of the materials mentioned above. In further embodiments, the disclosed implant is made of at least two different materials. Either material may constitute such as between 1 and 90 percent of the total volume of the entire implant. Thus, one material may constitute 1-10%, 10-20%, 20-30%, 30-40%, 40-50%, 50-60%, 60-70%, 70-80% or 80-90% of the total volume of the entire implant. The elements of the implant may comprise a central core of a metal surrounded by a layer of resorbable ceramic material. In further embodiments, the disclosed implant is made of at least three different materials.

The resilience of the material of the disc implant is preferably of an order similar to the resilience of bone. In addition, one or more elements or part of elements may be covered by a coating layer of a particular material in order to optimize function.

d. Coating

Coating of the implant can be performed to protect the implant from body fluids, including blood at the time of implantation as well as in a period followed implantation. A coating may alternatively or in addition be used for controlling bone growth in the vicinity of the implant by including suitable compounds.

In exemplary embodiments, the disclosed implant may be coated on the outer fusion surface, the internal coupling surfaces or the internal surface of the openings of the elements or any part of each surface or any combination of surfaces. In a preferred embodiment, the internal surface of the openings is coated.

The coating generally includes at least one layer of a coating material. The coating material may be selected from any suitable material. Thus, the coating may include osteoinductive and/or osteogenic agent(s) as described here below. The coating may also take the form of a suitable polymeric material, e.g., a material that minimizes metal-to-metal contact of the first and second inter-vertebral elements. The coating may further include one or more antibiotics.

By "coated" is meant that the coating material may be situated only on the outside of the coated surface. The thickness of the coating is generally selected based on the desired function and properties of the coating, and may have a thickness of less than 1 mm, less than 0.5 mm, or less than 0.25 mm. The thickness of the coating may also vary along the surface of the disclosed implant, e.g., at different surface points of the implant. The coating of the disclosed disc implants may be performed by any suitable coating method, e.g., by dipping the elements into a solution of the coating material for a predetermined time. The coating material may also be sprayed onto the implant; another possibility is to apply the said coating by brushing.

e. Coating Material

In exemplary embodiments of the present disclosure, one or more protective coatings may be provided on the disclosed spinal implants, the materials for such protective coating(s) being selected from, but not limited to, the group of polylactides (PLA's), polyglycolides (PGA's), polyanhydrides, polyorthoesters, poly(D,L-lactic acid), poly(lacide-co-glycolide) (PLGA), poly-D,L-lactic acid-polyyethylene glycol, polyphosphates, poly(lactide-co-glycolide) composited with gelatine sponge, poly(2-hydroxy ethyl methacrylate), poly(N-vinyl pyrrolidone), ethylene vinyl acetate (EVA), poly(methyl methacrylate), poly(vinyl alcohol), poly (acrylic acid), polyacrylamide, poly(ethylene-co-vinyl acetate), poly(ethylene glycol), poly(methacrylic acid), Homopolymers of L-PLA and poly-caprolactone (PCL), poly(orthoesters), like poly(anhydrides) and pseudo-poly (amino acids). The disclosed polymeric materials may advantageously limit and/or eliminate metal-to-metal contact between first and second inter-vertebral elements according to the present disclosure.

In further exemplary embodiments, the coating(s) may contain biologically active components, e.g. osteoinductive and/or osteogenic agent(s) (such as hydroxyapatite and/or tricalcium phosphate) or antibiotics. As examples, the inclusion of osteoinductive and/or osteogenic agents in the coating may induce early osteogenic processes, e.g., chemotaxis of specific cell classes, while the inclusion of antibiotics may reduce or prevent microbial infection.

Osteoinductive and/or osteogenic agents—which also can be denoted as and/or include "growth factors"—are generally proteins that bind to receptors on the cell surface, with the primary result of activating cell migration, cellular proliferation and/or differentiation. Many osteoinductive and/or osteogenic agents are quite versatile, stimulating cellular division in numerous different cell types, while others are specific to a particular cell-type.

Materials that are considered osteoinductive generally contain morphogens, such as bone morphogenetic proteins. Morphogens initiate tissue and organ system development by stimulating undifferentiated cells to convert phenotypically. Suitable growth factors which may be used according to the present disclosure include, but are not limited to, tissue growth enhancing substances, such as growth and differentiation factors, that include platelet-derived growth factor (PDGF), transforming growth factor (TGF), acidic and basic fibroblast growth factor (FGF), insulin-like growth factor (IGF), bone morphogenetic proteins (BMPs) and combinations thereof.

In exemplary embodiments of the present disclosure, the osteoinductive and/or osteogenic agent may be selected from the group of bone growth factors: platelet-derived growth factor (PDGF) (PDGF-AA, -AB, -BB), insulin-like growth factors I and II (IGF-I, IGF-II), fibroblast growth factors (FGFs) (acidic FGF-aFGF, basic FGF-bFGF), transforming growth factor beta (TGF-B) (TGF-B (TGF-Bs 1, 2, 3, 4, and 5)), osteoinduction and bone morphogenetic protein (BMP) (BMP-1, BMP-2, BMP-3, BMP-4, BMP-5, BMP-6, BMP-7, BMP-8, BMP-9, BMP-10, BMP-11, BMP-12), epidermal growth factor (EGF), cementum-derived growth factor (CGF), parathyroid hormone-related protein (PTHrP). Preferred growth factors or osteoinductive and/or osteogenic agents include the bone morphogenetic proteins (BMP-1, BMP-2, BMP-3, BMP-4, BMP-5, BMP-6, BMP-7, BMP-8, BMP-9, BMP-10, BMP-11, BMP-12) and platelet-derived growth factors (PDGF) (PDGF-AA, -AB, -BB).

Coatings for use according to the present disclosure may include at least one osteoinductive and/or osteogenic agent, and optionally more than one such agent, e.g., 2 agents, 3 agents, 4 agents, 5 agents, 6 agents, 7 agents, 8 agents, 9 agents, 10 agents or more. Exemplary implementations of the present disclosure include 1, 2 or 3 osteoinductive and/or osteogenic agents. More preferred implementations include 1 or 2 osteoinductive and/or osteogenic agents.

One or more layers of the coating material may be placed on or applied to the disclosed implant. In implementations where two or more layers are placed/applied, these layers may be equal or different in composition and one or more layers may contain osteoinductive and/or osteogenic agent (s) or other biologically active components.

Alternatively, the osteoinductive and/or osteogenic agents may be comprised of one or more of the materials forming the elements of the disclosed disc implant. Thus, the implant may be designed for secretion of one or more of the osteoinductive and/or osteogenic agents, whereby stimulation of bone growth is directed by or otherwise initiated/supported by the elements of the disc implant. The disclosed disc implant preferably encourages bone formation.

f. Osseointegrative Section(s)/Opening(s)

The first and second inter-vertebral elements of the disclosed disc implants generally include and/or define osseointegrative sections. Such sections generally have a capacity for stimulating and directing bone growth. For example, the inter-vertebral elements may be adapted to stimulate bone growth for fusion of the outer surface of each such inter-vertebral element relative to the neighboring vertebral element(s). The disclosed inter-vertebral elements are also generally adapted to further direct bone in-growth for fixation of the inter-vertebral elements relative to each other.

The inner and outer surface of the first and second inter-vertebral elements may include and/or define osseointegrative sections designed for optimization of bone in-growth according to the present disclosure. As described here below, the osseointegrative sections may be defined, in whole or in part, by openings, such as holes and/or incisions in the surface of the inter-vertebral elements which provide entry points for bone in-growth. The osseointegrative sections may also include suitable osteoinductive and/or osteogenic agents, and/or osteoinductive and/or osteogenic materials. Implementations of the present disclosure where openings formed in the intervertebral elements include osteoinductive and/or osteogenic agents, and/or osteoinductive and/or osteogenic materials within such openings are referred to as "filled" openings.

In exemplary embodiments of the present disclosure, the disclosed inter-vertebral elements include or define one or more openings suitable for bone in-growth, such openings being sufficiently large to (i) allow entrance of osteoblasts and osteogenic cells and (ii) sustain the viability of such osteoblasts and osteogenic cells. The openings generally proceed or extend through the disclosed inter-vertebral elements and allow in-growth of bone through the elements. The openings may have any shape or size compatible with the design/geometry of the inter-vertebral elements of the disc implant. For example, the openings may constitute or define straight (or substantially straight) channels that extend through the inter-vertebral element(s). In exemplary embodiments, the diameter(s) of the opening(s) may vary as the channel extends through the inter-vertebral element, e.g., the diameter of the opening channels may be expanded with an internal void in the element.

The surface area of the intervertebral elements occupied by the openings is generally sufficient to support desired levels of bone in-growth to achieve fixation of the first and second intervertebral elements relative to each other over time. However, it is noted that such bone in-growth is generally not limited to bone growth through such openings, but is complemented by bone in-growth that extends along or around the outer edges of the inter-vertebral elements. In exemplary embodiments of the present disclosure, the openings occupy at least 5% of the surface area of the first and/or second intervertebral element(s), and in further exemplary embodiments, at least 10% or at least 15% of such surface are in order to permit/stimulate sufficient in-growth of bone. In further exemplary embodiments, the surface area of the first and/or second inter-vertebral element(s) that is occupied by the openings/holes is 10-40% of such surface area, e.g., 20-35% thereof. The openings and the internal void volume may constitute 10-90% of the bulk volume of the inter-vertebral elements of the disclosed disc implants, e.g., 20-80%, 30-70%, 40-60% and/or 30-60% of the bulk volume of the inter-vertebral elements.

When referring to the bulk volume of the inter-vertebral elements, the volume of the coupling zone is not included, but merely the approximate volume of the individual inter-vertebral elements, including the volume of the openings and internal void volume, if present.

In exemplary embodiments of the present disclosure, the one or more openings of the first and second inter-vertebral elements are opposing each other, i.e., substantially aligned, when the inter-vertebral elements are engaged with each other via the coupling means/mechanism. An opposed/aligned arrangement of such openings provides optimal conditions for promoting bone in-growth though both inter-vertebral elements to achieve desired objects of the present disclosure, e.g., fusion of the disc implant at each outer surface relative to adjacent vertebral bodies and fixation of the first and second inter-vertebral elements of the disc implant elements relative to each other when bone tissue is formed in the coupling zone formed/defined by the internal surfaces of the inter-vertebral elements.

Minor openings on the surface of one or both inter-vertebral elements may be denoted as "pores", which affect the capabilities of the implant to stimulate bone growth at the surfaces. The level of porosity, pore size distribution, pore morphology, and the degree of pore interconnectivity of implants significantly influences the extent of bone growth. An exemplary pore volume on the outer surface of the first and/or second inter-vertebral body to encourage osteoinduction is 150-500 mm3. In addition, the outer surfaces of one or both inter-vertebral elements may further be rough, rugged or granular to further promote fusion relative to adjacent vertebral bodies.

g. Incisions/Circumferential Inset Regions

Alternative to or in combination with openings as described above, the disclosed inter-vertebral element(s) may include or define incisions or circumferential inset regions of various shapes/geometries to facilitate bone in-growth and fixation of the first and second inter-vertebral elements over time. Thus, in exemplary embodiments of the present disclosure, openings in and through the intervertebral elements may be combined with incisions/circumferential inset regions to promote/facilitate desired levels of bone in-growth. For example, the disclosed openings and incisions/circumferential inset regions may stimulate osteoconduction by providing a scaffold for the cells to move into and create new bone.

As noted above, the inter-vertebral elements of the disclosed disc implant may be fabricated from one or more different materials. In exemplary embodiments of the present disclosure, a filling may be located in the openings and/or incisions/circumferential inset regions of the intervertebral elements of the disc implant, whereby a filled implant is obtained. The filling may include material(s) suitable for directing and/or stimulating osteogenic activity and or inhibition of bone resorption. For example, auto and/or allograft of bone or demineralized bone matrix (DBM) may be used as a filling material. Artificial bone materials, such as ceramic materials, may also be employed. Resorbable materials, such as resorbable ceramic granules, may also be utilized, allowing and/or facilitating bone formation in the openings and/or incisions/circumferential inset regions within a suitable time. Thus, the disclosed spinal implant may be filled with resorbable materials, such as resorbable ceramic granules, which by suitable packaging may aid in the timing and/or extent of bone in-growth. In further exemplary embodiments, the filling may include osteoinductive and/or osteogenic agent(s), as described in relation to coatings.

h. Fusion of Implant

The spinal disc implant according to the present disclosure advantageously fuses with the surrounding vertebrae. In particular, the outer fusion surface of the first and second inter-vertebral elements are suited for fusion with neighboring bones/vertebral bodies. The elements of the disclosed disc implant are constructed to stimulate osteoconduction, i.e., the channeling of bone growth through the inter-vertebral elements of the implant. This bone in-growth leads to fixation of the first and second inter-vertebral elements relative to each other. In an exemplary embodiment of the present disclosure, fixation of the first and second inter-vertebral elements relative to each other—leading to the formation of a fixed implant—is caused at least in part by bone in-growth which occurs predominantly through the osseointegrative section(s) of the inter-vertebral elements of the disc implant.

i. Methods of Treatment

An individual suffering from lower back pain and/or leg pain resulting from spine injury or other disease may obtain relief by an insertion of a disc implant. An aspect of the present disclosure relates to method(s) of treatment of an individual in need thereof, wherein the method includes insertion of a disc implant. The disclosed method(s) may be achieved through anterior, lateral, posterior and or transforaminal insertion. In addition, the disclosed method(s) may be combined with insertion/implantation (or pre-existing) posterior stabilization means/devices. The posterior stabilization can be in form of flexible (dynamic), semi-rigid or rigid implants, such as pedicle screws, interspinous process spacers or facet joint screws or any other fixation/stabilization method known or subsequently developed in the art.

The first and second inter-vertebral elements may be introduced simultaneously, i.e., in a "pre-assembled" configuration. Alternatively, the first and second inter-vertebral elements may be introduced sequentially, with side-by-side assembly/positioning of the first and second inter-vertebral elements being undertaken and/or achieved in situ. To the extent a third element, e.g., a polymeric sheet or block, is positioned between the first and second inter-vertebral elements, such intermediate third element may be positioned relative to the first and/or second inter-vertebral element prior to anatomical positioning of the implant in the desired spinal location, or may be introduced sequentially, e.g., after the first and/or second inter-vertebral element is introduced to the anatomical location.

Although the present disclosure has been described with reference to exemplary embodiments thereof, the present disclosure is not limited by or to such exemplary embodiments. Rather, various modifications, refinements and/or changes may be made with reference to the spinal plates disclosed herein without departing from the spirit or scope thereof. For example, as one skilled in the art would immediately appreciate from the present disclosure, with the mating of the top and bottom elements as described, a variety of top and bottom elements could be designed and provided. For example, the length of the plates could be varied, as well as the number of screw holes. These variations would enable treatment of different anatomical sizes. The present disclosure expressly encompasses these and other modifications, refinements and/or changes, as will be apparent to persons skilled in the art.

The invention claimed is:

1. An implant assembly, comprising:
   a. a superior implant that includes an upstanding flange and a first intervertebral element extending from the upstanding flange, wherein the superior implant further includes (i) a first opening bounded by at least one arcuate boundary wall and defining a first axis, and (ii) a second opening formed in the upstanding flange configured and dimensioned for receipt of a locking member and defining a second axis; and
   b. an inferior implant that includes a flange portion and a second intervertebral element extending from the flange portion, wherein the second intervertebral element further includes an upstanding tab that defines at least one arcuate face and that is configured and dimensioned for receipt in the first opening of the superior implant;
   wherein the second axis of the second opening (i) passes through the upstanding tab and (ii) intersects with the first axis of the first opening.

2. The implant assembly according to claim 1, wherein the upstanding tab defines opposed arcuate faces.

3. The implant assembly according to claim 1, wherein the upstanding tab is interleaved with respect to the at least one arcuate boundary wall when the superior implant is assembled with respect to the inferior implant.

4. The implant assembly according to claim 1, wherein the upstanding tab of the inferior implant and the first opening bounded by the at least one arcuate boundary wall of the superior implant accommodate flexion/extension rotational freedom of movement as between the inferior implant and the superior implant until such time as the superior implant and the inferior implant are fixed relative to each other.

5. The implant assembly according to claim 1, wherein the upstanding flange and the flange portion include cooperating arcuate faces.

6. The implant assembly according to claim 1, wherein the upstanding flange includes at least one aperture to facilitate mounting of the superior implant element relative to an anatomical structure.

7. The implant assembly according to claim 1, wherein the flange portion includes at least one aperture to facilitate mounting of the inferior implant element relative to an anatomical structure.

8. The implant assembly according to claim 1, wherein the second opening is threaded.

9. The implant assembly according to claim 1, further comprising a locking member configured and dimensioned for cooperation with the second opening.

10. The implant assembly according to claim 1, wherein the first intervertebral element and second intervertebral element include openings that permit bone ingrowth.

\* \* \* \* \*